(12) United States Patent
Zeng et al.

(10) Patent No.: US 8,765,819 B2
(45) Date of Patent: Jul. 1, 2014

(54) COMPOSITION COMPRISING BENZOIC ACID IN COMBINATION WITH ORGANIC ACID PRESERVATIVES AS ACTIVE INGREDIENTS AND THE USE THEREOF

(76) Inventors: Zhongming Zeng, Guangdong (CN); Ruyun Zhou, Guangdong (CN)

( * ) Notice: Subject to any disclaimer, the term of this patent is extended or adjusted under 35 U.S.C. 154(b) by 0 days.

(21) Appl. No.: 13/501,020

(22) PCT Filed: Oct. 8, 2010

(86) PCT No.: PCT/CN2010/001552
§ 371 (c)(1),
(2), (4) Date: Jun. 18, 2012

(87) PCT Pub. No.: WO2011/041938
PCT Pub. Date: Apr. 14, 2011

(65) Prior Publication Data
US 2012/0245132 A1    Sep. 27, 2012

(30) Foreign Application Priority Data
Oct. 8, 2009    (CN) .......................... 2009 1 0179633

(51) Int. Cl.
*A01N 31/00* (2006.01)
*A61K 31/45* (2006.01)
*A61K 9/00* (2006.01)
*A61K 31/192* (2006.01)

(52) U.S. Cl.
CPC .................. *A61K 9/0034* (2013.01);
*A61K 31/192* (2013.01)
USPC ......................................... 514/730; 514/739

(58) Field of Classification Search
None
See application file for complete search history.

(56) References Cited

U.S. PATENT DOCUMENTS

| 3,600,198 | A | * | 8/1971 | Gonthier ...................... 426/335 |
| 7,906,140 | B2 | | 3/2011 | Bromley et al. |
| 2003/0017207 | A1 | | 1/2003 | Lin et al. |
| 2006/0105008 | A1 | | 5/2006 | Ahmad et al. |
| 2008/0193428 | A1 | | 8/2008 | Zhou et al. |
| 2009/0304813 | A1 | | 12/2009 | Hickok |

FOREIGN PATENT DOCUMENTS

| CN | 1522145 A | 8/2004 |
| CN | 1688329 A | 10/2005 |
| CN | 101005828 B | 7/2007 |
| CN | 101437504 A | 5/2009 |
| CN | 101744833 B | 6/2010 |
| EP | 1 911 454 A1 | 4/2008 |
| WO | 2006114061 A1 | 11/2006 |

OTHER PUBLICATIONS

Federal Register, Proposed Rules, Oct. 13, 1983, p. 46704, vol. 48, No. 199.
Rui-yun, Ji, et al., "Progress in the Treatment of Vaginitis", J Int Obstet Gynecol, 2009, pp. 307-315, vol. 36, No. 4.
Dermatological Drugs (topical), World Health Organization, Archived Jul. 8, 2008, http://archives.who.int/eml/wmf/2004/English/Dermatological_drugs._topical.pdf.
Niiya et al., On the Antifungal Effect of Preservatives in Margarine (II), Food Hygiene and Safety Science, 1969, pp. 393-N/A, vol. 10, No. 6, Japan, (Abstract).
Puttanna, Mycotic Infections of the Cornea, Indian Journal of Opthalmology, 1967, pp. 11-18, vol. 15, issue 1, http://www.ijo.in/text.asp?1967/15/1/11/38672.
Alter, Robert L. et al., "The Treatment of Mycotic Vulvovaginitis with Propionate Vaginal Jelly", American Journal of Obstetrics and Gynecology, Feb. 1947, vol. 53, No. 2, pp. 241-244.
Brown, Dale Jr., "Therapeutic Alternatives and New Treatment Modalities in Vulvovaginal Candidiasis" Journal of Reproductive Medicine, 1986, vol. 31, No. 7, pp. 653-654.
Stedman, R.L. et al., "In Vitro Antimicrobial Activity of a Dehydroacetic Acid and p-Chlor-m-xylenol Combination", Journal of the American Pharmaceutical Association, 1954, vol. 43, No. 10, pp. 622-624.

* cited by examiner

*Primary Examiner* — James D Anderson
*Assistant Examiner* — William Lee
(74) *Attorney, Agent, or Firm* — The Webb Law Firm

(57) ABSTRACT

The present invention relates to the use of low content of benzoic acid and/or sodium salt thereof in combination with one or more organic acid preservatives as active ingredients in the manufacture of a vaginal composition, wherein the composition has weak inhibition effect on normal vaginal lactobacilli while has strong inhibition effect on vaginal fungi and/or pathogenic vaginal lactobacilli, the organic acid preservatives are selected from the group consisting of dehydroacetic acid and/or sodium salt thereof, propionic acid and/or a salt thereof, sorbic acid and/or a salt thereof. The composition of the present invention is particularly useful in inhibiting vaginal fungi, and/or inhibiting pathogenic vaginal lactobacilli, and/or promoting normal vaginal lactobacilli, and/or maintaining normal vaginal acidity, and/or modulating vaginal microecosystem, and/or modulating vaginal microbials, and/or selectively decontaminating vagina.

14 Claims, No Drawings

COMPOSITION COMPRISING BENZOIC ACID IN COMBINATION WITH ORGANIC ACID PRESERVATIVES AS ACTIVE INGREDIENTS AND THE USE THEREOF

TECHNICAL FIELD

The present invention relates to a vaginal composition and the manufacture use thereof, wherein the composition has weak inhibition effect on normal vaginal lactobacilli while has strong inhibition effect on vaginal fungi and/or pathogenic vaginal lactobacilli. The composition of the present invention is particularly useful in inhibiting vaginal fungi, and/or inhibiting pathogenic vaginal lactobacilli, and/or promoting normal vaginal lactobacilli, and/or maintaining normal vaginal acidity, and/or modulating vaginal microecosystem, and/or modulating vaginal microbials, and/or selectively decontaminating vagina.

BACKGROUND ART

The female vaginal mucous surface is suitable for microorganisms such as bacteria, fungi, etc. to inhabit. The dominant bacteria inhabited on healthy vaginal mucous surface are large Gram-positive rods, usually called "vaginal normal flora". Most of these large Gram-positive rods belong to the category of lactobacilli, and are mainly lactobacilli. They are capable of producing acids by metabolizing glycogen in vaginal mucous epithelial cells so as to maintain the vaginal acidity within a pH value range from 3.5 to 4.5, preferably from 3.8 to 4.1. The vaginal acidity plays a very important role in the health of female genital tract and in the resistance of infections caused by pathogenic bacteria. Once abnormal changes in the vaginal flora and acidity occur, the chance of vaginal infection caused by various pathogenic bacteria is greatly increased.

Many factors may disturb vaginal flora and vaginal acidity so as to reduce the capability of resisting infections caused by pathogenic bacteria in female vagina. Thereby, vaginal microbial diseases are common in women.

Among vaginal microbial diseases, Candidal vaginitis, bacterial vaginosis (BV), cytolytic vaginosis (CV), and atrophic vaginitis (AV) are most common. They are all associated with the pathological change in vaginal acidity. As reported in a document, if a patient has the symptoms such as vulvovaginal pruritus and vulvovaginal burning pain and a vaginal pH value of from 4.0 to 4.5, the patient is diagnosed to have a high probability of suffering from Candidal vaginitis[1], if a patient has the symptoms such as vulvovaginal pruritus and vulvovaginal burning pain and a vaginal pH value of 4.0 or below, the patient is diagnosed to have a high probability of suffering from cytolytic vaginosis[1]. The inventors found after researches that the vaginal pH is mostly 4.0 or below, in particular, 3.8 or below in cytolytic vaginitis, and the pH is mostly 4.5 below, in particular 4.1 below in Candidal vaginitis. Therefore, when the vaginal pH is 4.0 or below, the patient might suffer from either Candidal vaginitis or cytolytic vaginitis. If a patient has the discomforts such as vulvovaginal pruritus and fishy smell and a vaginal pH value of 4.5 or above, the patient is diagnosed to have a high probability of suffering from bacterial vaginosis[2]. The vaginal pH is also greater than 4.5 in atrophic vaginitis.

After researches, the inventors found out that Candidal vaginitis, in particular, recurrent refractory Candidal vaginitis, are mainly endogenous infection. In acidic microenvironment formed by acids produced by vaginal lactobacilli, fungi (represented by Candida) overgrow and produce toxin, and therefore cause vaginal inflammations. In fact, most of the vaginal floras in these patients are dominated by lactobacilli. The characteristic is especially prominent in the case of recurrent, refractory candidal vaginitis. The Candidal hyphae or spores could be found in the patient's vaginal secretion. The pH value of vaginal secretion is usually below 4.5 and even lower than 4.1. The clinical symptoms include vulvovaginal pruritus, vulvovaginal burning pain, urodynia, algopareunia, etc. The symptoms are usually most serious before menstruation and alleviated during and after menstruation. The current therapeutic methods include the administration of various antifungal agents or antibiotics such as ketoconazole, nystatin, etc.

Cytolytic vaginosis are also associated with the overgrowth of vaginal lactobacilli, the over-production of acids by vaginal lactobacilli, and the too low pH value in vagina. Large and long Gram-positive rods are observable in vaginal secretion, while Candidal hyphae or spores could not be found. Usually, the vaginal acidity of patient is over-high, and the pH value of vaginal secretion is below 4.0 in general. The clinical symptoms are similar to those of Candidal vaginitis, including vulvovaginal pruritus, vulvovaginal burning pain, urodynia, algopareunia, etc., which usually are most serious before menstruation and are obviously alleviated during and after menstruation, as periodic episode. Therapeutic methods mainly include the demibain with alkali solution of sodium bicarbonate to neutralize the high acidity of vaginal secretion, and the administration of antibiotics Augmentin (Amoxicillin+Clavulanic acid) to inhibit lactobacilli.

Bacterial vaginosis is associated with the decrease of vaginal lactobacilli and the reduction of vaginal acidity. The pH value in vagina is higher than 4.5, the overgrowth of many microorganisms including anaerobic bacteria, etc. causes "polymicrobial syndrome". The clinical symptoms include discomforts such as vulvovaginal pruritus, fishy smell leucorrhea, etc. Atrophic vaginitis is associated with the decrease of vaginal lactobacilli and the reduction of vaginal acidity, and is generally characterized by discomforts such as vulvovaginal pruritus, vulvovaginal pain etc.

The current methods for treatment of above vaginal microbial diseases mainly relate to inhibiting or killing microbials, for example, Candidal vaginitis is treated by inhibiting and/or killing fungi with antifungal agents selected from fluconazol, nystatin, clotrimazole, etc. Cytolytic vaginosis is treated by killing lactobacilli with antibacterial agents Augmentin, etc. Bacterial vaginosis is treated by killing anaerobic bacteria with metronidazole, etc.

After years of research and clinical practice, the inventors of the present invention found that said antibacterial treatments inhibit or kill pathogenic bacteria whilst killing normal vaginal lactobacilli and disrupting vaginal acidity, resulting in the reduction of the natural vaginal resistance against infection, and then the enhancement of pathogenic bacteria colonization, and thereby causing recurrent infection or persistent infection. How to avoid the disruption of normal vaginal lactobacilli and acidity and protect the natural anti-infection barrier in vagina during the treatment of vaginal infections is an unsolved problem for a long time. It is also a common problem confronted by microbial killing or inhibiting methods for treating various vaginal infectious diseases.

In the patent application PCT/CN2006/000826, the inventors of the present invention had disclosed a composition comprising saccharides and benzoic acid and/or sodium salt thereof as active ingredients for modulating vaginal bacterial flora and vaginal acidity, wherein saccharides are capable of promoting lactobacilli, and benzoic acid and/or sodium salt thereof significantly inhibit lactobacilli when the vaginal acidity is over-high. The composition of that invention promotes the growth of vaginal lactobacilli and the acid production of lactobacilli when vagina lactobacilli are rare and the vaginal acidity is weak, and inhibits the acid production of lactobacilli when the vaginal acidity is over-high, and therefore returns the abnormal vaginal bacterial flora into the normal bacterial flora dominated by lactobacilli and maintains the vaginal acidity within the range from 3.5 to 4.5, preferably from 3.8 to 4.1. The composition comprising anti-fungal agents mentioned therein is applied to the treatment of Candidal vaginitis. However, it is not mentioned that benzoic acid and/or sodium salt thereof itself has a preventive or therapeutic effect on Candidal vaginitis. Moreover, it is not mentioned that low content of benzoic acid and/or sodium salt thereof in combination with organic acid preservatives such as low content of dehydroacetic acid and/or sodium salt thereof, and/or low content of propionic acid and/or sodium salt thereof, and/or low content of sorbic acid and/or sodium salt thereof, etc. has a synergistic effect on the inhibition of vaginal fungi.

Low content of benzoic acid and/or sodium salt thereof as preservative is widely used in food and medicine manufacture field, its effective concentration as preservative is generally 0.1~0.2% in an oral or external preparation[3], sodium benzoate as preservative generally has a concentration of 0.5% in a neutral or subacid pharmaceutical preparation[4]; tinctures or ointments comprising benzoic acid at a high concentration of 6~12% are useful in the treatment of tinea of feet and hands[5]. However, neither compositions comprising benzoic acid and/or sodium salt thereof alone, especially benzoic acid and/or sodium salt thereof at a low content of 0.2% or below as active ingredient, nor the vaginal compositions comprising low content of benzoic acid and/or sodium salt thereof in combination with low content of other organic acid preservatives as active ingredients, are disclosed.

Propionic acid and/or a salt thereof, and sorbic acid and/or a salt thereof, as therapeutic agent, at a high concentration, are useful in alleviation of vaginal discomforts. U.S. FDA shows in Federal Register/Vol. 48, No. 199, 46704/Oct. 12, 1983/Proposed Rules that propionate (calcium salt or sodium salt) at a single dose of up to 2.3 g and a concentration of up to 20% is safe and effective in a vaginal preparation, and has an inhibition effect on fungi and Gram-positive cocci; in addition, another document shows that propionate sodium has a medicinal concentration of 5% in eye drops and a medicinal concentration of 5~10% in anti-fungal solutions[6], the vaginal compositions comprising 0.5% or less propionic acid or a salt thereof as active ingredient are not disclosed.

Dehydroacetic acid is generally used as anti-tinea agent, and has a good inhibition effect on many pathogenic fungi at a concentration of from 0.05 to 0.5%[7]. However, it is not disclosed that dehydroacetic acid or a salt thereof at a concentration of less than 0.05% is applied to against the pathogenic fungi.

U.S. FDA shows in Federal Register/Vol. 48, No. 199, 46704/Oct. 13, 1983/Proposed Rules that vaginal lotions comprising 1~3% potassium sorbate are regarded to be safe and effective. The vaginal compositions comprising 1%, or even 0.1% or less of sorbic acid or a salt thereof as active ingredient are not disclosed.

To sum up, there is no report on an antibacterial (bacteriostatic) composition comprising low content of benzoic acid and/or sodium salt thereof in combination with organic acid preservatives, such as low content of dehydroacetic acid and/or sodium salt thereof, and/or low content of propionic acid and/or a salt thereof, and/or low content of sorbic acid and/or a salt thereof, as active vaginal ingredients.

SUMMARY OF THE INVENTION

The object of the present invention is to provide a vaginal composition, wherein the composition has weak inhibition effect on normal vaginal lactobacilli while has strong inhibition effect on vaginal fungi and/or pathogenic vaginal lactobacilli.

Another object of the present invention is to provide a vaginal composition for inhibiting vaginal fungi, and/or inhibiting pathogenic vaginal lactobacilli, and/or promoting normal vaginal lactobacilli, and/or maintaining normal vaginal acidity, and/or modulating vaginal microecosystem, and/or modulating vaginal microbials, and/or selectively decontaminating vagina.

The further object of the present invention is to provide a vaginal composition for eliminating or alleviating discomforts such as vulvovaginal pruritus, vulvovaginal pain, and/or algopareunia, and/or improving leucorrhea nature, and/or eliminating the odor of leucorrhea, and/or cleaning-nursing vagina.

The composition according to the present invention is useful for prevention and/or treatment of vaginal microbial diseases selected from the group consisting of Candidal vaginitis, cytolytic vaginosis, vaginal dysbacteriosis, and atrophic vaginitis.

In order to study the methods for modulating vaginal flora, the inventors have conducted a lot of researches in vivo and in vitro for many years. It is found that although in the patent document PCT/CN2006/000826 the composition comprising saccharides in combination with benzoic acid and/or sodium salt thereof as active ingredients is capable of two-ways modulation of vaginal flora and vaginal acidity, i.e., promoting the growth of lactobacilli and the acid production of lactobacilli when the lactobacilli in vagina are rare and the vaginal acidity is over-weak, and inhibiting the acid production of lactobacilli when the lactobacilli in vagina are abundant and the vaginal acidity is over-strong, there is still the risk of secondary overgrowth of vaginal fungi as well as fungal infections. After a lot of research and accumulation, the inventors have further discovered the characteristics of benzoic acid and/or sodium salt thereof in vivo, i.e., it significantly inhibits the vaginal lactobacilli at a dose or concentration that is effective to inhibit vaginal fungi, typically Candida; and it fails to effectively inhibit vaginal fungi at a dose or concentration that has no significant inhibition effect on vaginal lactobacilli. Therefore, the inventors have improved the technical solution of PCT/CN2006/000826 so as to confer the anti-fungal effects upon the vaginal composition while keeping its' two-ways modulation action on vaginal flora and vaginal acidity.

Through repeated researches on the active characteristics of preservatives at different concentrations and the interaction among different bacteriostats, the inventors were surprised to find that, although it was reported in the prior art that the inhibition effect of benzoic acid against beer yeast might be antagonized by preservatives such as formic acid, sorbic acid, Nipagin esters, etc.[8], it shows by experiments that the combination of benzoic acid with dehydroacetic acid, or with sorbic acid, or with propionic acid, etc. has synergistic effect in inhibiting Candida under acidic condition of low pH value (such as a pH value of 4.5).

In particular, it is surprisingly found that, contrary to the common sense of professionals that large dose or high concentration of preservatives are needed for therapeutic use, benzoic acid and/or sodium salt thereof in combination with organic acid preservatives such as dehydroacetic acid, etc. has strong inhibition effect on Candida at low dose or low concentration. Moreover, it is also found that such anti-bacterial activity is highly associated with pH value: when the pH value of vaginal secretion is 4.5 or above, it has an inhibition effect on Candida, but has less inhibition effect on lactobacilli; when the pH value is 4.1 or around, its inhibition effect on vaginal Candida is enhanced; when the vaginal pH value is 3.8, in particular, when the vaginal pH value is 3.5 or below, it has a stronger inhibition effect on Candida and meanwhile has a significant inhibition effect on lactobacilli.

The present invention has been accomplished by the inventors based on the above discovery and further studies. In the composition and the method of present invention, benzoic acid and/or sodium salt thereof in combination with specific organic acid preservative are used successfully as active ingredients, and the organic acid preservative is used at a low dose/low concentration for a therapeutic use, while the combination achieves selective inhibition on vaginal fungi and/or pathogenic lactobacilli without significantly inhibiting or disrupting normal vaginal lactobacilli. It is of great theoretical and practical significance in clinical therapeutics. Thus the combination can be used to prepare vaginal compositions for promoting normal vaginal lactobacilli, and/or maintaining the vaginal acidity, and/or inhibiting vaginal fungi, and/or inhibiting pathogenic vaginal lactobacilli, so as to prevent and/or treat various vaginal microbial diseases or diseases associated with microecosystem, and for daily cleaning and nursing of vagina in females. Thus, it has an extensive future.

In the technical solutions according to the present invention, low content of benzoic acid and/or sodium salt thereof in combination with specific organic acid preservative as active ingredients has weak inhibition effect on normal vaginal lactobacilli but has strong inhibition effect on vaginal fungi and/or pathogenic vaginal lactobacilli. The organic acid preservatives according to the present invention are selected from the group consisting of dehydroacetic acid and/or sodium salt thereof, propionic acid and/or a salt thereof, sorbic acid and/or a salt thereof; wherein the propionic acid salt is a calcium salt or sodium salt thereof, preferably sodium salt thereof; and the sorbic acid salt is a potassium salt thereof or sodium salt thereof, preferably, sodium salt thereof.

The composition of the present invention can be used to inhibit vaginal fungi, and/or to inhibit pathogenic vaginal lactobacilli, and/or to promote normal vaginal lactobacilli, and/or to maintain normal vaginal acidity, and/or to modulate vaginal microecosystem, and/or to modulate vaginal microbials, and/or to selectively decontaminate vagina.

In preferred embodiments, the composition of the present invention is useful in eliminating or alleviating discomforts such as vulvovaginal pruritus, vulvovaginal burning pain, and/or algopareunia, and/or in improving leucorrhea nature, and/or in eliminating the odor of leucorrhea, and/or in cleaning-nursing vagina. The composition of the present invention is particularly useful for the prevention and/or treatment of vaginal microbial diseases, wherein the vaginal microbial diseases are selected from the group consisting of Candidal vaginitis, lactobacillosis, cytolytic vaginosis, vaginal dysbacteriosis, and atrophic vaginitis.

In the technical solutions according to the present invention, the combination of low content of benzoic acid and/or sodium benzoate with low content of dehydroacetic acid and/or sodium salt thereof, and/or propionic acid and/or a salt thereof, and/or sorbic acid and/or a salt thereof as active ingredients, has strong inhibition effect on vaginal fungi at a vaginal pH value of 4.1 or below (such as pH 3.8-4.1); and it does not only have a stronger inhibition effect on vaginal fungi but also have a significant inhibition effect on the acid production of lactobacilli at a vaginal pH value below 3.8, in particular at a pH of 3.5 or below; and therefore, it does not only inhibit vaginal fungi but also inhibit the pathogenic vaginal lactobacilli for over-producing acids. Thus, it is particular suitable for maintaining the balance of vaginal microecosystem, and is suitable for the manufacture of a medicament for prevention and/or treatment of Candidal vaginitis, and/or a medicament for prevention and/or treatment of lactobacillosis and cytolytic vaginosis caused by pathogenic lactobacilli, and/or a medicament for modulating various vaginal microecosystems, and/or a nursing product for vaginal microecosystem, and/or a vagina-cleaning product and a sanitary product.

In the technical solutions according to the present invention, the compositions are useful for vaginal administration as microecosystem modulator, microbial modulator, medicine, disinfectant, antibacterial agent, bacteriostatic agent, mucous topical microbicide, or disposable medical product; or are ingredients for a vaginal use disinfecting device, medical device, or medicine device, and etc.; or are useful for vaginal administration as sanitary product, cosmetic, nursing product for vaginal microecosystem, cleaning-nursing product, deodorizing agent, lubricant, humectant, or lotion. In the technical solutions according to the present invention, the compositions include but are not limited to the following vaginal dosage forms: solutions, ointments (preferably water-soluble gel and emulsion ointments), effervescent tablets, capsules, microcapsules, suppositories, or tablets, or are ingredients of vaginal disinfecting devices, medical devices, or medicine devices, and so on; preferably water-soluble gels, capsules, tablets, or aqueous solutions.

According to the technical solutions of the present invention, the composition preferably comprises the following amount of each of the ingredients per unit administration dose or unit dosage form: the total amount of benzoic acid and/or sodium salt thereof, calculated based on sodium benzoate, is 0.25~10 mg, preferably 0.5~6.25 mg; a organic acid preservative or a salt thereof, selected from the group consisting of: dehydroacetic acid and/or sodium dehydroacetate, the total amount of which, calculated based on sodium dehydroacetate, is 0.025~2.5 mg, preferably 0.05~1.25 mg per unit dosage form; propionic acid and/or a salt thereof, the total amount of which, calculated based on sodium propionate, is 0.5~50 mg, preferably 1.0~25 mg per unit dosage form; sorbic acid and/or a salt thereof, the total amount of which, calculated based on sodium sorbate, is 0.05~5 mg, preferably 0.1~2.5 mg per unit dosage form. The selection of the preparation process, methods and adjuvants can be envisaged by a person skilled in the art according to the contents disclosed in the present invention in combination with the background art.

According to the technical solutions of the present invention, when the composition is in a form of solution or ointment (preferably water-soluble gel and emulsion ointment), the total amount of benzoic acid and/or sodium benzoate, calculated based on sodium benzoate, is 0.025~0.2% (w/v), preferably 0.05~0.125% (w/v); a organic acid preservative or a salt thereof, selected from the group consisting of: dehydroacetic acid and/or sodium salt thereof, the total amount of which, calculated based on sodium dehydroacetate, is 0.0025~0.05% (w/v), preferably 0.005~0.025% (w/v); propionic acid and/or a salt thereof, the total amount of which, calculated based on sodium propionate, is 0.05~1.0% (w/v), preferably 0.1~0.5% (w/v); sorbic acid and/or a salt thereof, the total amount of which, calculated based on sodium sorbate, is 0.005~0.1% (w/v), preferably 0.01~0.05% (w/v). The selection of the preparation process, methods and adjuvants can be envisaged by a person skilled in the art according to the content disclosed in the present invention in combination with the background art.

For example, a gel composition can be prepared preferably by using a water-soluble gel matrix, most preferably Xanthan gum, according to the following process flow based on the methods known by those skilled in the art: homogeneously mixing specific proportions of sodium benzoate, an organic acid preservative or a salt thereof selected from the group consisting of dehydroacetic acid and/or sodium salt thereof, propionic acid and/or a salt thereof, sorbic acid and/or a salt thereof, as well as Xanthan gum; adding distilled water quantitively; stirring to dissolve the ingredients and to swell the Xanthan gum to form a homogenous viscous gel; adjusting the pH value of the composition to a prescribed value, by using an acid and/or base; further sterilizing by a process selected from: radiation sterilization, or high-temperature sterilization (for example, at 115.6° C. for 15-20 minutes, or at 100° C. for 30 minutes), or fractional sterilization (for example, firstly treating at 80° C. for 30 minutes and then at 36° C. for 5-10 hours, treating at 80° C. for 30 minutes and then at 36° C. for 5-10 hours again, and finally treating at 80° C. for 30 minutes), or filtering and sterilizing separately the solution of the ingredient such as benzoic acid and/or its sodium salt and the like and then adding them into a sterilized water-soluble gel matrix.

For example, a solution composition can be prepared by mixing the ingredients except for water-soluble gel matrix, adding water, dissolving the ingredients, sterilizing for further use; cotton balls or tampons are soaked with the solution for vaginal administration or the solution can be formulated into a vaginal lotion.

Vaginal tablets can be prepared according to the methods known by those skilled in the art, for example, the methods introduced in Pharmaceutics edited by Xi Nianzhu and Gu Xueqiu[9], i.e., mixing benzoic acid and/or sodium salt thereof, organic acid preservatives or the salts thereof, and the filling adjuvants in a prescribed proportion, and then directly tableting to obtain tablets, wherein adjuvants such as magnesium stearate as lubricant or sodium carboxymethyl starch as disintegrant can also be added, mixed homogeneously, and tableted. The prepared tablets can be packaged in a drug delivery device, a disinfecting device, a medical device or a medicine device.

Vaginal suppositories can be manufactured according to the following process flow based on the methods known by those skilled in the art[10]: homogeneously mixing and grinding quantative amount of benzoic acid and/or sodium salt thereof, organic acid preservative or a salt thereof selected from the group consisting of dehydroacetic acid and/or sodium salt thereof, propionic acid and/or a salt thereof, sorbic acid and/or a salt thereof, as well as Tween 80; heating to about 50° C.; heating separately a mixed fatty glyceride (also called: Solid Fat) to 60° C. until melting, then adding the mixture liquid of the benzoic acid and/or sodium salt thereof, the organic acid preservative or a salt thereof and Tween 80 to the melting matrix under stirring, mixing homogeneously, pouring into a mould at about 40° C. (i.e., before coagulation), cooling slightly and scraping the mould, cooling and demolding to obtain the vaginal suppositories. Preferably, the matrix of the said suppositories is mixed fatty glyceride, propylene glycol stearate, glycerogelatin, Tween 61, etc., more preferably the mixed fatty glyceride. Automatic and mechanical devices can be used in large scale production. The prepared suppositories can be packaged in a drug delivery device, a disinfecting device, a medical device or a medicine device.

The water soluble gel composition can be prepared by using a non-flowable, viscous, water-soluble gel matrix, which enables the composition to homogenously contact with vaginal mucosa and remain there for a relatively long time, thereby play its role. The said water-soluble gel matrix is selected and used according to the knowledge of those skilled in the art. According to the present invention, the matrix is preferably Xanthan gum or poly-carbophil, and more preferably Xanthan gum.

When preparing a water-soluble gel or solution composition, the pH value is adjusted within the range from 3.5 to 6.5, preferably 4.0 to 5.5 by acids or bases. The selection of the type and concentration of the acid or base for adjusting the pH value of the said composition is within the knowledge of those ordinary skilled in the art. Hydrochloric acid, phosphoric acid and sodium hydroxide are preferred.

The organic acid preservative or a salt thereof used in the present invention is present in the forms of unionized molecules or ionized ions after being dissolved in water. The ratio of unionized molecules and ionized ions depends on the pH value of the solution and the ionization constant $PK_a$. When $pH=PK_a$, each of the ratio of the organic acid molecules and the organic acid ions is 50%; when $pH>PK_a$, the number of organic acid ions is greater than the number of organic acid molecules; and when $pH<PK_a$, the number of unionized organic acid molecules is greater than the number of organic acid ions. Therefore, since both the organic acid preservative and the salt thereof are present in the forms of organic acid molecules or organic acid ions after being dissolved in water, they have no substantial difference.

The antibacterial effect of an organic acid preservative is associated with the concentration of the unionized organic acid molecules. The higher the concentration, the stronger the antibacterial effect is. When the composition of the present invention is administrated to vagina, the lower the pH value of the vaginal secretion is, the higher the concentration of organic acid molecules in vagina is, and then the stronger the inhibition effect thereof will be on vaginal fungi and/or pathogenic lactobacilli.

In the present invention, low content of benzoic acid and/or sodium salt thereof in combination with organic acid preservatives, is characterized in selectively inhibiting vaginal fungi and/or pathogenic lactobacilli, and has a weak inhibition effect on normal vaginal lactobacilli. It can be further combined with amino acids as active ingredients to prepare a composition capable of modulating the metabolism of vaginal lactobacilli and reducing the acid production, wherein benzoic acid and/or sodium salt thereof in combination with organic acid preservative selectively inhibits the acid production of pathogenic lactobacilli, and enhances the action of amino acids on the acid production caused by the metabolism of lactobacilli. Therefore, the composition is suitable for prevention and/or treatment of diseases caused by the overproduction of acids by pathogenic lactobacilli and overstrong vaginal acidity, such as Candidal vaginitis, cytolytic vaginosis, or lactobacillosis.

To the compositions of the present invention, one or more amino acids and/or a salt thereof can be added, wherein the amino acids are selected from the group consisting of glutamic acid, glutamine, aspartic acid, asparagine, isoleucine, phenylalanine, valine, leucine, proline, threonine or a mixture thereof; preferably glutamic acid, aspartic acid or a mixture thereof; wherein the amino acids are present at such an amount that, the total amount of the amino acids is 0.03~1.75 mmol, preferably 0.08~1 mmol per unit administration dosage form or per single dose package (i.e., unit dosage form) of the composition, such as a tablet, a suppository or an ointment packaged in a single dose.

In the technical solution of the present invention, low content of benzoic acid and/or sodium salt thereof in combination with organic acid preservatives, is characterized in selectively inhibiting vaginal fungi and/or pathogenic lactobacilli, and has a weak inhibition effect on normal vaginal lactobacilli. It can be further combined with saccharides as active ingredients to prepare a composition for promoting the growth and acid-production of vagainal normal lactobacilli, wherein benzoic acid in combination with organic acid preservatives prevents lactobacilli from acid production excessively caused by metabolism after using the saccharide-containing composition, and therefore significantly reduce the overly strong vaginal acidity subsequent to the using of saccharide-containing composition, and reduce the incidence of subsequent adverse side effects, such as overgrowth of fungi and fungal infection. A composition comprising benzoic acid and/or sodium salt thereof, organic acid preservative and saccharide is suitable for prevention and/or treatment of diseases with decreased lactobacilli and reduced vaginal acidity, such as bacterial vaginosis, vaginal dysbacteriosis, atrophic vaginitis, and the like.

The compositions according to the present invention, may further optionally comprise one or more saccharides selected from the group consisting of glucose, fructose, mannose, sucrose, maltose, isomaltose, trehalose, cellobiose, melibiose, raffinose, panose, malto-oligosaccharide, fructo-oligosaccharide, dextrin, starch, glycogen, or a mixture thereof; the preferred saccharide is glucose, fructose, mannose, sucrose, maltose, trehalose, or a mixture thereof. The saccharide is present in such an amount that, the total amount of the saccharide is 1~750 mg, preferably 60~600 mg per unit administration dosage form or per single dose package (i.e., unit dosage form) of the composition, such as a tablet, a suppository or an ointment packaged in a single dose.

The compositions according to the present invention, may further optionally comprise low content of antibacterial agents such as metronidazole or tinidazole, wherein the metronidazole or tinidazole is present in such an amount that, the total amount of metronidazole and/or tinidazole is 0.001~0.5 mg, preferably 0.01~0.25 mg per unit administration dosage form or per single dose package (i.e., unit dosage) of the composition, such as a tablet, a suppository or an ointment packaged in a single dose. The metronidazole or tinidazole within such concentration range has a weak antibacterial activity against lactobacilli and has a strong inhibitory activity against anaerobic bacteria, i.e., inhibiting anaerobic bacteria without inhibiting lactobacilli, and therefore would be especially helpful to make lactobacilli to be the dominant flora in vagina again. Thus, the composition of the present invention comprising low content of metronidazole or tinidazole has the effect of nursing and/or modulating microecosystem, resisting fungi, resisting anaerobic bacteria and maintaining the balance of microecosystem.

The compositions according to the present invention may further optionally comprise estrogens, and the compositions are also useful for prevention and/or treatment of Atrophic vaginitis, wherein the estrogens is present at such an amount that the total amount of one or more estrogens, selected from the group consisting of stilbestrol, estradiol and/or estriol, preferably estriol, is 0.01~3 mg per unit administration dosage form or per single dose package (i.e., unit dosage form) of the composition, such as a tablet, a suppository or an ointment packaged in a single dose.

The present invention further provides a vaginal ointment (preferably water soluble gel and emulsion ointment) or solution composition, characterized in:

(1) comprising benzoic acid and/or sodium salt thereof as active ingredients, the total concentration of which, calculated based on sodium benzoate, is 0.025~0.2% (w/v), preferably 0.05~0.125% (w/v);

(2) comprising dehydroacetic acid and/or sodium salt thereof, and/or propionic acid and/or a salt thereof, and/or sorbic acid and/or a salt thereof as active ingredients; wherein the total concentration of dehydroacetic acid and/or sodium salt thereof, calculated based on sodium dehydroacetate, is 0.0025~0.05% (w/v), preferably 0.005~0.025% (w/v); the total concentration of propionic acid and/or a salt thereof, calculated based on sodium propionate, is 0.05~1.0% (w/v), preferably 0.1~0.5% (w/v); the total concentration of sorbic acid and/or a salt thereof, calculated based on sodium sorbate, is 0.005~0.1% (w/v), preferably 0.01~0.05% (w/v);

(3) comprising ointment matrix in a form of emulsion, water-soluble gel matrix, or water; preferably non-flowable, viscous, water-soluble gel matrix (water-soluble unguent bases); particularly and preferably Xanthan gum;

(4) the pH value of the composition is from 3.5 to 6.5, preferably from 4.0 to 5.5.

The composition may be in the form of packaged with many kinds of manners, including but not limited to, single dose with sterilized and sealed package, or packaged in a vagina use device, or packaged in a disposable vagina use device; preferably single dose with sterilized and sealed package.

The ointment or solution compositions according to the present invention are preferably in a dosage form of non-flowable, viscous, water-soluble gel. The compositions may further optionally comprise one or more amino acids and a salt thereof, selected from the group consisting of glutamic acid, glutamine, aspartic acid, asparagines, isoleucine, phenylalanine, valine, leucine, proline, threonine or a mixture thereof; preferably glutamic acid, aspartic acid or a mixture thereof, at a total concentration of 30~350 mmol/L; the preferred total concentration of the amino acid is 80~200 mmol/L.

The ointment or solution compositions according to the present invention, may further optionally comprise one or more saccharides at a total concentration of 0.1~15% (w/v), selected from the group consisting of glucose, fructose, mannose, sucrose, maltose, isomaltose, trehalose, cellobiose, melibiose, raffinose, panose, malto-oligosaccharide, fructo-oligosaccharide, dextrin, starch, glycogen, or a mixture thereof; the preferred saccharide is glucose, fructose, mannose, sucrose, maltose, trehalose or a mixture thereof; the preferred total concentration of the saccharide is 6.0~12% (w/v).

The ointment or solution compositions according to the present invention, may further optionally comprise metronidazole or tinidazole at a total concentration of 0.1~10 mg % (w/v), preferably metronidazole or tinidazole at a total concentration of 1~5 mg % (w/v).

The ointment or solution compositions according to the present invention, may further optionally comprise one or more estrogens at a total concentration of 0.001~0.06% (w/v), selected from the group consisting of stilbestrol, estradiol and/or estriol; preferably, estriol.

The ointment or solution compositions of the present invention may be in the form of packaged with many kinds of manners, including but not limited to, single dose with sterilized and sealed package, or packaged in a vaginal use device such as a vaginal use disinfecting device, medical device, or medicine device, or packaged in a disposable vaginal use device; preferably single dose with sterilized and sealed package. The sterilization process well known by those skilled in the art can be used for sub-packaging and sealing the sterilized or sterilization-treated composition, or for sub-packaging and sealing the prepared composition and then sterilizing, or sub-packaging the prepared composition in a disposable device for intra-vaginal administration, or packaging in a device for vaginal use such as a medical device for vaginal use, sealing with overwrap, then sterilizing by radiation, and etc.

The present invention especially relates to a method for promoting normal vaginal lactobacilli, and/or maintaining normal vaginal acidity, and/or inhibiting vaginal fungi, and/or inhibiting pathogenic vaginal lactobacilli, wherein the method comprises administration of an active amount of the vaginal composition prepared according to the manufacture use of the present invention to a female in need thereof.

Since penicillin was successfully applied to the clinical treatments about 60 years ago, large doses of antibacterial agents are required in clinical therapeutics in antimicrobial treatment to thoroughly eliminate or inhibit pathogenic microorganisms. After conducting researches and clinical practices for many years, the inventors found that although such therapeutic methods may quickly eliminate or inhibit pathogenic bacteria, they meanwhile greatly disrupt the normal bacterial flora in human bodies and would cause a series of adverse effects, such as disruption of colonization resistance, colonization of drug-resistant bacteria, superinfection and the like. After long-term religious and elaborative researches and practices, the inventors finally gave up the strategy of "thoroughly eliminating or inhibiting" pathogenic microbes, and invented a unique antimicrobial method of "low dose, finiteness and selectivity", which selectively inhibits vaginal fungi and/or pathogenic vaginal lactobacilli, and/or inhibits other vaginal pathogenic microbes, reduces their proliferation rate, decrease their amount, protect and/or promote the growth of normal vaginal lactobacilli, makes lactobacilli to be the dominant flora in vagina again, and returns the vaginal acidity back into the normal range.

With regard to organic acid preservatives for therapeutic use, according to the common knowledge well known in the professional field, large doses are required. For example, the conventional dose of propionic acid salts for inhibiting vaginal fungi and Gram-positive cocci and treating vaginal discomforts is up to 2.3 g each time, and the concentration is up to 20%[11]. However, in the method according to the present invention, the organic acid preservative is present at a low dose, which is equivalent to the dose used in foods or drugs for preservation. For example, in the method according to the present invention, the amount of sodium propionate for each time is 50 mg at most. The former is nearly 50 folds of the latter.

In the technical solutions according to the present invention, the composition is administrated to the vagina of a female in need thereof. For example, a gel composition is administrated to the vagina by an administration device, or cotton ball or tampon soaked with the solution composition of the present invention is placed in vagina, or a composition of the present invention in the form of suppository or tablet is directly administrated to vagina, 1 to 3 times daily, each course for 3 to 10 days, preferably 4 to 7 days. During the treatment, changes in patient's symptoms should be observed and the pH value of vagina should be determined. If the patient's symptoms are significantly improved or eliminated and the pH value of vagina is kept within a range of 3.8 to 4.1, the administration will be discontinued or the administration amount will be decreased.

The method of the present invention solves the problem of how to effectively resist vaginal fungi and inhibit the overproduction of acids by pathogenic vaginal lactobacilli very well, whilst protecting the physiological function of vaginal microescosystem, avoiding the disruption of normal physiological vaginal lactobacilli. The method for prevention and/or treatment vaginal microbial diseases according to the present invention, comprises intravaginal administration of an effective amount of the composition prepared according to the manufacture use of the present invention to a female in need thereof, wherein the vaginal microbial diseases are Candidal vaginitis, cytolytic vaginosis, lactobacillosis, bacterial vaginosis, vaginal dysbacteriosis, or atrophic vaginitis.

The method according to the present invention is useful in eliminating or alleviating discomforts such as vulvovaginal pruritus, vulvovaginal burning pain, or algopareunia, or improving leucorrhea nature, or eliminating the odor of leucorrhea, or cleaning vagina, or nursing and/or modulating vaginal microecosystem, the method comprising intravaginal administration of an effective amount of the compound of the present invention to a female in need thereof.

EMBODIMENTS OF INVENTION

Composition Examples

Example 1

0.1 g sodium benzoate, 0.0075 g sodium dehydroacetate and 2.5 g Xanthan gum were mixed homogeneously. 100 ml distilled water was added. Stirred, Sodium benzoate and sodium dehydroacetate were dissolved, and Xanthan gum was swollen to form a homogenous viscous gel. The pH value of the solution was adjusted to 5.0. Sterilization was carried out at 115.6° C. for 15 minutes to obtain the water-soluble gel composition of the present invention.

Example 2

By weighing the materials with the following proportion, 100 ml composition was made substantially according to the method of Example 1.

| sodium benzoate | 0.2% (w/v) |
| sodium dehydroacetate | 0.005% (W/V) |
| glucose | 1.5% (w/v) |
| Xanthan gum | 2.5% (w/v) |
| distilled water | 100 ml |
| pH | 5.0 |

Example 3

By weighing the materials with the following proportion, 100 ml composition was made substantially according to the method of Example 1.

| sodium benzoate | 0.025% (w/v) |
| sodium dehydroacetate | 0.05% (w/v) |
| trehalose | 9.0% (w/v) |
| Xanthan gum | 2.0% (w/v) |
| distilled water | 100 ml |
| pH | 5.5 |

Example 4

By weighing the materials with the following proportion, 100 ml composition was made substantially according to the method of Example 1.

| | |
|---|---|
| sodium benzoate | 0.1% (w/v) |
| sodium dehydroacetate | 0.005% (w/v) |
| maltose | 9% (w/v) |
| Xanthan gum | 2.5% (w/v) |
| distilled water | 100 ml |
| pH | 5.0 |

Example 5

By weighing the materials with the following proportion, 100 ml composition was made substantially according to the method of Example 1.

| | |
|---|---|
| sodium benzoate | 0.1% (w/v) |
| sodium dehydroacetate | 0.0125% (W/V) |
| Xanthan gum | 2.5% (w/v) |
| distilled water | 100 ml |
| pH | 4.5 |

Example 6

By weighing the materials with the following proportion, 100 ml composition was made substantially according to the method of Example 1.

| | |
|---|---|
| sodium benzoate | 0.1% (w/v) |
| sodium dehydroacetate | 0.0125% (W/V) |
| glutamic acid | 50 mmol |
| aspartic acid | 30 mmol |
| Xanthan gum | 2.5% (w/v) |
| distilled water | 100 ml |
| pH | 4.5 |

Example 7

By weighing the materials with the following proportion, 100 ml composition was made substantially according to the method of Example 1.

| | |
|---|---|
| sodium benzoate | 0.1% (w/v) |
| sorbic acid | 0.0125% (w/v) |
| Xanthan gum | 2.5% (w/v) |
| distilled water | 100 ml |
| pH | 4.5 |

Example 8

By weighing the materials with the following proportion, 100 ml composition was made substantially according to the method of Example 1.

sodium benzoate 0.2 g, sodium propionate 0.125 g;
glutamic acid 3.0 mmol, glutamine 3.0 mmol, aspartic acid 3.0 mmol, asparagine 3.0 mmol, isoleucine 3.0 mmol, methionine 3.0 mmol, phenylalanine 3.0 mmol, valine 3.0 mmol, leucine 3.0 mmol, proline 3.0 mmol;
Xanthan gum 2.5 g, distilled water 100 ml, pH being adjusted to 4.5.

Example 9

By weighing the materials with the following proportion, 100 ml composition was made substantially according to the method of Example 1.

| | |
|---|---|
| sodium benzoate | 0.1% (w/v) |
| sodium propionate | 0.125% (w/v) |
| Xanthan gum | 2.5% (w/v) |
| distilled water | 100 ml |
| pH | 4.5 |

Example 10

According to conventional processes in the art, a tablet comprising sodium benzoate 6.25 mg, sodium dehydroacetate 1.25 mg, magnesium stearate 5 mg, 25 mg sodium carboxymethyl starch, microcrystalline cellulose 462.5 mg was prepared. The ingredients above were mixed in proportion homogeneously and then were directly tableting to obtain tablets.

Example 11

According to conventional processes in the art, a vaginal suppository comprising sodium benzoate 6.25 mg, sodium dehydroacetate 1.25 mg, 14 mg Tween-80, and solid fat 478.5 mg was prepared.

Example 12

According to conventional processes in the art, the following solution was prepared:

| | |
|---|---|
| sodium benzoate | 0.2% (w/v) |
| sodium propionate | 1.0% (W/V) |
| pH | 4.5 |

Experimental Example

Experimental Example I

1. Experimental Object: observing the synergistic inhibition effects of the compositions comprising the combination of benzoic acid and/or sodium salt thereof with the preservatives of the present invention on vaginal Candida. Unless otherwise illustrated, the solutions in the experiments are all aqueous solutions.

2. Experimental Method:
(1) Experimental Materials:
a) Experimental strains: 11 Candida strains, all of which were screened from the clinical isolates from patients suffering from Candidal vaginitis, and were capable of growing in broth comprising 0.025% (w/v) sodium benzoate.
b) Broth: 1% yeast extract powder, 9% sucrose, 0.025% Manganese sulfate ($MnSO_4.4H_2O$), 0.058% Magnesium sulphate ($MgSO_4.7H_2O$), and 0.9% lactic acid, wherein the pH value was adjusted to 4.5 and the broth was sterilized for use;
(2) Experimental Grouping:
The requirements for aseptic technique were strictly followed to prepare the following groups of sterile test tubes:

a) sodium benzoate group: a test tube containing 5 ml broth, to which 0.025% (w/v) sodium benzoate was added;
b) sodium benzoate+sodium dehydroacetate group: 6 test tubes each containing 5 ml broth, wherein 0.0025% (w/v), 0.005% (w/v), and 0.01% (w/v) sodium dehydroacetate were added to three tubes, respectively; 0.025% (w/v) sodium benzoate was added to each of the rest 3 tubes, and then 0.0025% (w/v), 0.005% (w/v), 0.01% (w/v) sodium dehydroacetate were added to them, respectively;
c) sodium benzoate+sodium propionate group: 6 test tubes each containing 5 ml broth, wherein 0.0625% (w/v), 0.125% (w/v), and 0.25% (w/v) sodium propionate were added to three tubes, respectively; 0.025% (w/v) sodium benzoate was added to each of the rest 3 tubes, and then 0.0625% (w/v), 0.125% (w/v), and 0.25% (w/v) sodium propionate were added to them, respectively;
d) sodium benzoate+potassium sorbate group: 6 test tubes each containing 5 ml broth, wherein 0.00625% (w/v), 0.0125% (w/v), and 0.025% (w/v) potassium sorbate were added to 3 tubes, respectively; 0.025% (w/v) sodium benzoate was added to each of the rest 3 tubes, and then 0.00625% (w/v), 0.0125% (w/v), and 0.025% (w/v) potassium sorbate were added to them, respectively;
e) sodium benzoate+Ethylparaben: 6 test tubes each containing 5 ml broth, wherein 0.0125% (w/v), 0.025% (w/v), and 0.05% (w/v) Ethylparaben were added to 3 tubes, respectively; 0.025% (w/v) sodium benzoate was added to each of the rest 3 tubes, and then 0.0125% (w/v), 0.025% (w/v), and 0.05% (w/v) Ethylparaben were added to them, respectively;
f) Positive control: a broth-containing test tube with Candida but without sodium benzoate, sodium dehydroacetate, sodium propionate, sorbic acid, or Ethylparaben.
g) Negative control: a broth-containing test tube without Candida, sodium benzoate, sodium dehydroacetate, sodium propionate, sorbic acid, or Ethylparaben;

(3) Experimental Methods:

The Candidal suspensions were prepared under stringent aseptic manipulation techniques. The colonies of various Candidal strains were diluted with saline, respectively. The turbidity was adjusted with a turbiditor to 0.5M (about $10^8$CFU/ml), and then 1 ml 0.5M bacterial solution was added to 9 ml broth and was 10 times diluted, so that each Candidal suspension comprised Candidal organisms at $10^7$CFU/ml.

Under stringent aseptic manipulation techniques, 100 μl bacterial solution thus prepared was added to each of the aforesaid a~f test tubes and the positive control tube, and no bacterial solution was added to the negative control tube g.

These tubes were incubated in a biochemical incubator at 37.5° C. for 72 hours. The turbidity of the test tubes were observed and recorded.

3. Results (1) The inhibition effect of sodium benzoate on Candida: 0.025% (w/v) sodium benzoate alone could not inhibit the growth of the test strains, as all the test strains (11/11) grew after incubation and all the test tubes turned turbid, and they were identified as Candida spores under microscopic examination of the stained smear.

(2) Synergistic effect: sodium benzoate 0.025% (w/v) in combination with the preservatives had the following inhibition effect on Candida:

① The inhibition effect of sodium dehydroacetate on Candida: as shown in Table 1, with the increasing of the concentration of sodium dehydroacetate, its inhibition effect on Candida enhanced. In the tube containing 0.0025% (w/v) sodium dehydroacetate, 10 of the 11 strains grew; in the tube containing 0.01% (w/v) sodium dehydroacetate, 7 of the 11 strains grew; in the tube containing 0.025(w/v) sodium benzoate and 0.0025% (w/v) sodium dehydroacetate, 9 of the 11 Candida strains grew; in the tube containing 0.025% (w/v) sodium benzoate and 0.01% (w/v) sodium dehydroacetate, 3 of the 11 Candida strains grew;

② The inhibition effect of sodium propionate on Candida: in the tube containing 0.0625% (w/v) sodium propionate, all the 11 strains grew; in the tube containing 0.25% (w/v) sodium propionate, 5 of the 11 Candida strains grew; in the tube containing 0.025% (w/v) sodium benzoate and 0.0625% (w/v) sodium propionate, 8 of the 11 Candida strains grew; in the tube containing 0.025% sodium benzoate (w/v) and 0.25% (w/v) sodium propionate, none of the 11 strains grew;

③ The inhibition effect of potassium sorbate on Candida: in the tube containing 0.00625% (w/v) potassium sorbate, 10 of the 11 strains grew; in the tube containing 0.025% (w/v) potassium sorbate, 9 of the 11 Candida strains grew; in the tube containing 0.025(w/v) sodium benzoate and 0.00625% (w/v) potassium sorbate, 8 of the 11 Candida strains grew; in the tube containing 0.025% (w/v) sodium benzoate and 0.025% (w/v) potassium sorbate, 5 of the 11 strains grew.

④ The inhibition effect of Ethylparaben on Candida: in the tube containing 0.0125% (w/v) Ethylparaben, all the 11 strains grew; in the broth containing 0.05% (w/v) Ethylparaben, 8 of the 11 Candida strains grew; in the tube containing 0.025% (w/v) sodium benzoate and 0.0125% (w/v) Ethylparaben, 10 of the 11 strains grew; in the tube containing 0.025% (w/v) sodium benzoate and 0.05% Ethylparaben, 7 of the 11 Candida strains grew.

⑤ In the positive control tube without any organic acid preservatives, Candidal organisms grew, and in the negative control tube containing broth alone without adding Candida organisms, no any organisms grew.

4. Conclusion: sodium benzoate in combination with sorbic acid, sodium propionate or sodium dehydroacetate, had a different degree of synergistic effect on Candida strains isolated from vagina at pH4.5; however, sodium benzoate in combination with Ethylparaben has no significant synergistic effect on Candida.

TABLE 1

The inhibition effect of sodium benzoate in combination with organic acid preservative on *Candida*

| Strain | 1 | 2 | 3 | 4 | 5 | 6 | 7 | 8 | 9 | 10 | 11 |
|---|---|---|---|---|---|---|---|---|---|---|---|
| 0.025% sodium benzoate | + | + | + | + | + | + | + | + | + | + | + |
| 0.0025% sodium dehydroacetate | + | + | + | + | − | + | + | + | + | + | + |
| 0.005% sodium dehydroacetate | + | + | + | + | − | + | + | + | − | + | + |
| 0.01% sodium dehydroacetate | + | − | + | + | − | + | + | + | − | + | − |
| 0.0025% sodium dehydroacetate + 0.025% sodium benzoate | + | + | + | + | − | + | + | + | + | + | − |
| 0.005% sodium dehydroacetate + 0.025% sodium benzoate | − | + | + | + | − | − | + | + | − | + | − |

TABLE 1-continued

The inhibition effect of sodium benzoate in combination with organic acid preservative on *Candida*

| Strain | 1 | 2 | 3 | 4 | 5 | 6 | 7 | 8 | 9 | 10 | 11 |
|---|---|---|---|---|---|---|---|---|---|---|---|
| 0.01% sodium dehydroacetate + 0.025% sodium benzoate | − | − | − | + | − | − | − | + | − | + | − |
| 0.0625% sodium propionate | + | + | + | + | + | + | + | + | + | + | + |
| 0.125% sodium propionate | + | + | + | + | − | + | + | + | − | + | − |
| 0.25% sodium propionate | − | − | + | + | − | − | + | + | − | + | − |
| 0.0625% sodium propionate + 0.025% sodium benzoate | + | + | + | + | − | + | + | + | − | + | − |
| 0.125% sodium propionate + 0.025% sodium benzoate | − | − | − | + | − | − | − | + | − | + | − |
| 0.25% sodium propionate + 0.025% sodium benzoate | − | − | − | − | − | − | − | − | − | − | − |
| 0.00625% potassium sorbate | + | + | + | + | + | + | + | + | − | + | + |
| 0.0125% potassium sorbate | + | − | + | + | + | + | + | + | − | + | + |
| 0.025% potassium sorbate | + | − | + | + | + | + | + | + | − | + | + |
| 0.00625% potassium sorbate + 0.025% sodium benzoate | + | − | + | + | + | − | + | + | − | + | + |
| 0.0125% potassium sorbate + 0.025% sodium benzoate | − | − | + | + | + | − | + | + | − | + | − |
| 0.025% potassium sorbate + 0.025% sodium benzoate | − | − | + | + | − | − | + | + | − | + | − |
| 0.0125% Ethylparaben | + | + | + | + | + | + | + | + | + | + | + |
| 0.025% Ethylparaben | + | + | + | + | + | + | + | + | + | + | + |
| 0.05% Ethylparaben | − | + | + | + | − | + | + | + | − | + | + |
| 0.0125% Ethylparaben + 0.025% sodium benzoate | + | + | + | + | − | + | + | + | + | + | + |
| 0.025% Ethylparaben + 0.025% sodium benzoate | − | + | + | + | + | + | + | + | − | + | + |
| 0.05% Ethylparaben + 0.025% sodium benzoate | − | − | + | + | − | + | + | + | − | + | + |
| Positive control tube | + | + | + | + | + | + | + | + | + | + | + |
| Negative control tube | − | − | − | − | − | − | − | − | − | − | − |

Note:
"+": Candidal organism grew; "−" no Candidal organism grew.

Experimental Example II

1. Experimental Object: observing the therapeutic effect of the compositions comprising the combination of sodium benzoate with sodium propionate or sorbic acid. Unless otherwise illustrated, the solutions in the experiments are all aqueous solutions.
2. Experimental grouping: the gel compositions comprising the following ingredients were made according to the method of Example 1, wherein all of the compositions had a pH of 4.5.
   Group I: 0.125% (w/v) sodium propionate;
   Group II: i.e., the composition of Example 9 comprising 0.1% (w/v) sodium benzoate+0.125% (w/v) sodium propionate;
   Group III: 0.0125% (w/v) sorbic acid;
   Group IV: i.e., the composition of Example 7 comprising 0.1% (w/v) sodium benzoate+0.0125% (w/v) sorbic acid;
   Group V: 0.1% (w/v) sodium benzoate;
   Group VI: i.e., the composition of Example 5 comprising 0.1% sodium benzoate+0.0125% sodium dehydroacetate.
3. Experimental cases: cases of Candidal vaginitis, 20 cases per group, enrolling according to following criteria: recurrent symptoms such as vulvovaginal pruritus and vulvovaginal burning pain, and increased leucorrhea, optionally with white bean curd slag-like clots, pH value of vaginal secretion <4.5, vaginal bacteria were dominated by large Gram-positive rods, and Candida spores and/or hypha were found.
4. Omission of cases: the cases, which failed to complete the treatment course, failed to reexamination, or washed vagina with or administrated with antibacterial agents during the observation, were omitted cases and were excluded from tests.
5. Experimental methods: the patients in the group were administrated topically in vagina with 5 g the composition of the present invention twice per day for consecutive 5 days, wherein the patients were at least administrated by the doctor once a day; the pH value of vaginal secretion was determined, microscopic examination of the stained secretion smear was conducted, the bacterial number and form were observed, and Nugent scoring was conducted.
6. Observed results: observing the changes in vulvovaginal pruritus, vulvovaginal burning pain and leucorrhea nature, the pH value of vaginal secretion, observing the Nugent scores of the vaginal flora, whether Candida grew or not.
7. Experimental result: as shown in Table 2,
   1) Group I: the composition comprising 0.125% sodium propionate reduced the vaginal acidity and increased the pH in the patients, the detection rate of Candida decreased from 20/20 to 11/20, discomforts such as vulvovaginal pruritus and vulvovaginal burning pain were alleviated, and the leucorrhea was improved.
   2) Group II: the composition comprising 0.1% sodium benzoate and 0.125% sodium propionate reduced the vaginal acidity and increased the pH in the patients, the detection rate of Candida significantly decreased from 20/20 to 2/20, discomforts such as vulvovaginal pruritus and vulvovaginal burning pain were alleviated and leucorrhea decreased, without bean curd slag-like clots.
   3) Group III: the composition comprising 0.0125% sorbic acid reduced the vaginal acidity and increased the pH in the patients, the detection rate of Candida decreased from 20/20 to 13/20, and discomforts such as vulvovaginal pruritus and vulvovaginal burning pain were alleviated.
   4) Group IV: the composition comprising 0.1% sodium benzoate and 0.0125% sorbic acid reduced the vaginal acidity and increased the pH in the patients, the detection rate of Candida significantly decreased from 20/20 to 4/20, discomforts such as vulvovaginal pruritus and vulvovaginal burning pain were alleviated and leucorrhea decreased, with very few bean curd slag-like clots.
   5) Group V: the composition comprising 0.1% sodium benzoate reduced the vaginal acidity and increased the pH in the patients, the detection rate of Candida decreased from 20/20 to 6/20, such as vulvovaginal pruritus and vulvovaginal burning pain were alleviated, and the leucorrhea decreased.
   6) Group VI: the composition comprising 0.0125% sodium dehydroacetate and 0.1% sodium benzoate reduced the vaginal acidity and increased the pH in the patients, the detection rate of yeast significantly decreased from 20/20 to 1/20, and leucorrhea decreased, without bean curd slag-like clots.

8. Conclusion: the composition of the present invention comprising sodium benzoate in combination with sodium dehydroacetate, or in combination with sodium propionate, or in combination with sorbic acid, inhibited vaginal fungi and vaginal lactobacilli, reduced the vaginal acidity moderately, alleviated or even eliminated the discomforts such as vulvovaginal pruritus and vulvovaginal burning pain, and had a therapeutic effect on Candidal vaginitis. The composition of the present invention comprising sodium benzoate and sodium dehydroacetate was superior to the composition comprising sodium dehydroacetate or sodium benzoate alone; the composition of the present invention comprising sodium benzoate in combination with sodium propionate had a better inhibition effect on Candida than the composition comprising sodium propionate or sodium benzoate alone; the composition of the present invention comprising sodium benzoate and sorbic acid had a better inhibition effect on Candida than the composition comprising sorbic acid or sodium benzoate alone.

TABLE 2

The therapeutic effect of the compositions on Candidal vaginitis

| | before administration | Day 1 | Day 2 | Day 3 | Day 4 | Day 5 | Result assessment |
|---|---|---|---|---|---|---|---|
| Group I: 0.125% sodium propionate | | | | | | | |
| symptom alleviated/eliminated | 0/20 | 7/20 | 9/20 | 14/20 | 13/20 | 13/20 | The symptoms were improved after administration of the composition; the pH of vagina was increased; the detection rate of *Candida* was low. |
| pH 4.2~4.5 | 5/20 | 5/20 | 6/20 | 9/20 | 9/20 | 8/20 | |
| pH 3.8~4.1 | 9/20 | 12/20 | 11/20 | 9/20 | 10/20 | 10/20 | |
| pH <3.8 | 6/20 | 3/20 | 3/20 | 2/20 | 1/20 | 2/20 | |
| *Candida* | 20/20 | 16/20 | 13/20 | 10/20 | 12/20 | 11/20 | |
| Group II: 0.125% sodium propionate + 0.1% sodium benzoate | | | | | | | |
| symptom alleviated/eliminated | 0/20 | 8/20 | 10/20 | 14/20 | 17/20 | 17/20 | The symptoms were improved after administration of the composition; the pH of vagina was increased; the detection rate of *Candida* was decreased. |
| pH 4.2~4.5 | 4/20 | 5/20 | 7/20 | 10/20 | 10/20 | 11/20 | |
| pH 3.8~4.1 | 9/20 | 12/20 | 12/20 | 8/20 | 9/20 | 8/20 | |
| pH <3.8 | 7/20 | 3/20 | 1/20 | 2/20 | 1/20 | 1/20 | |
| *Candida* | 20/20 | 12/20 | 5/20 | 3/20 | 2/20 | 2/20 | |
| Group III: 0.0125% sorbic acid | | | | | | | |
| symptom alleviated/eliminated | 0/20 | 6/20 | 12/20 | 11/20 | 13/20 | 12/20 | The symptoms were improved after administration of the composition; the pH of vagina was increased; the detection rate of *Candida* was low. |
| pH 4.2~4.5 | 6/20 | 6/20 | 7/20 | 8/20 | 8/20 | 7/20 | |
| pH 3.8~4.1 | 9/20 | 13/20 | 11/20 | 10/20 | 11/20 | 11/20 | |
| pH <3.8 | 5/20 | 1/20 | 2/20 | 2/20 | 1/20 | 2/20 | |
| *Candida* | 20/20 | 15/20 | 15/20 | 13/20 | 14/20 | 13/20 | |
| Group IV: 0.0125% sorbic acid + 0.1% sodium benzoate | | | | | | | |
| symptom alleviated/eliminated | 0/20 | 8/20 | 9/20 | 17/20 | 14/20 | 16/20 | The symptoms were improved after administration of the composition; the pH of vagina was increased; the detection rate of *Candida* was significantly decreased. |
| pH 4.2~4.5 | 5/20 | 7/20 | 9/20 | 11/20 | 10/20 | 10/20 | |
| pH 3.8~4.1 | 9/20 | 11/20 | 10/20 | 9/20 | 9/20 | 9/20 | |
| pH <3.8 | 6/20 | 2/20 | 1/20 | 0/20 | 1/20 | 1/20 | |
| *Candida* | 20/20 | 15/20 | 8/20 | 5/20 | 3/20 | 4/20 | |
| Group V: 0.1% sodium benzoate | | | | | | | |
| symptom alleviated/eliminated | 0/20 | 7/20 | 9/20 | 14/20 | 15/20 | 15/20 | The symptoms were improved after administration of the composition; the pH of vagina was increased; the detection rate of *Candida* was low. |
| pH 4.2~4.5 | 4/20 | 6/20 | 9/20 | 9/20 | 9/20 | 10/20 | |
| pH 3.8~4.1 | 10/20 | 12/20 | 10/20 | 9/20 | 10/20 | 9/20 | |
| pH <3.8 | 6/20 | 2/20 | 1/20 | 2/20 | 1/20 | 1/20 | |
| *Candida* | 20/20 | 15/20 | 13/20 | 9/20 | 5/20 | 6/20 | |

TABLE 2-continued

The therapeutic effect of the compositions on Candidal vaginitis

|  | before adminis- tration | Day 1 | Day 2 | Day 3 | Day 4 | Day 5 | Result assessment |
|---|---|---|---|---|---|---|---|
| Group VI: 0.0125% sodium dehydroacetate + 0.1% sodium benzoate |  |  |  |  |  |  |  |
| symptom alleviated/eliminated | 0/20 | 8/20 | 12/20 | 17/20 | 18/20 | 18/20 | The symptoms were improved after |
| pH 4.2~4.5 | 6/20 | 7/20 | 10/20 | 12/20 | 13/20 | 11/20 | administration of the |
| pH 3.8~4.1 | 9/20 | 12/20 | 10/20 | 8/20 | 7/20 | 9/20 | composition; the pH of |
| pH <3.8 | 5/20 | 1/20 | 0/20 | 0/20 | 0/20 | 0/20 | vagina was increased; |
| *Candida* | 20/20 | 15/20 | 9/20 | 6/20 | 3/20 | 1/20 | the detection rate of *Candida* was significantly decreased. |

Note:
symptoms improved/eliminated: discomforts such as vulvovaginal pruritus and vulvovaginal burning pain are significantly improved or eliminated, leucorrhea decreases, with very few or without bean curd slag-like clots.
The normal pH range of vagina is from 3.5 to 4.5, preferably 3.8~4.1. When the pH is below 3.8, the acidity is over-enhanced.
Vaginal *Candida*: normal for negative.

Experimental Example III

1. Experimental object: observing the therapeutic effect on Bacterial vaginosis of the compositions comprising the combination of sodium benzoate, organic acid preservative and saccharides. Unless otherwise illustrated, the solutions in the experiments are all aqueous solutions.
2. Experimental agents: the following compositions, whose pH was 5.0, were made substantially according to the method of Example 1.
   Group I: 9% (w/v) maltose;
   Group II: 9% (w/v) maltose+0.5% (w/v) sodium benzoate;
   Group III: 9% (w/v) maltose+0.2% (w/v) sodium benzoate;
   Group IV: 9% (w/v) maltose+0.1% (w/v) sodium benzoate;
   Group V: i.e. the composition of Example 4, comprising 9% (w/v) maltose+0.1% (w/v) sodium benzoate+0.005% (w/v) sodium dehydroacetate;
   Group VI: 0.1% (w/v) sodium benzoate+0.005% (w/v) sodium dehydroacetate;
   Group VII: 9% (w/v) maltose+0.1% (w/v) sodium benzoate+0.1% (w/v) sodium propionate;
   Group VIII: 9% (w/v) maltose+0.1% (w/v) sodium benzoate+0.0125% (w/v) sorbic acid.
3. Experimental cases: cases of Bacterial vaginosis, 10 cases for Group VI, and for the rest groups, 16 cases per group, enrolling according to following criteria:
(1) Clinical symptoms: abnormal leucorrhea, may optionally accompanied with discomforts such as vulvovaginal pruritus, leucorrhea with fishy smell, vulvovaginal burning pain, or algopareunia;
(2) microscopic examination of the stained secretion smear: a lot of bacteria in different shapes were found, and multiple Gram-negative rods, cocci and Gram-positive cocci were dominant; however, large Gram-positive rods were not found or were occasional, Nugent score >7;
(3) pH value of vaginal secretion >4.6;
(4) microscopic examination of vaginal secretion, leukocyte/pyocyte <10 at high magnification;
(5) No antibacterial treatment in 2 weeks.
4. Omission of cases: the cases, which failed to complete the treatment course according to the requirements, or administrated with antibacterial/antifungal agents during the treatment course, were excluded from tests.
5. Experimental methods: the patients in the groups were administrated topically in vagina with 5 g the composition of the present invention twice per day for consecutive 5 days, wherein the patients were at least administrated by the doctor once a day; the pH value of vaginal secretion was determined, microscopic examination of the stained secretion smear was conducted, the bacterial number and forms were observed, and Nugent scoring was conducted, wherein Nugent score of 3 or below: normal vaginal flora; Nugent score of 4-6: intermediate BV; Nugent score of 7 or above: typical Bv.
6. Observed results: the omitted cases were excluded, observing changes in the symptoms such as abnormal leucorrhea, fishy smell, vulvovaginal pruritus and the like, whether the pH value of vaginal secretion is lower than 4.5 or not, whether the Nugent scores of the vaginal flora is 3 or below, and whether Candida grew or not.
7. Experimental result: as shown in Table 3

Group I: the composition comprising maltose alone had a strong effect of promoting the growth of lactobacilli, vaginal lactobacilli was quickly restored after using it, 13/14 cases had an Nugent score of vaginal flora ≤3; vaginal acidity rapidly reduced, a part of cases (5/14) had a vaginal pH reduced to 3.8 below; the ratio of the cases with overgrowth of fungi was high (9/14). After administration of the composition for two days, vulvovaginal pruritus was significantly alleviated, leucorrhea decreased, and fishy smell disappeared in the patients, however, after administration of the composition for three days, discomforts such as vulvovaginal pruritus reoccurred in a part of patients.

Group II: the composition comprising maltose and 0.5% sodium benzoate had a strong inhibition effect on vaginal fungi, and no overgrowth of vaginal fungi was observed in the cases after using it; however, the composition also had a strong inhibition effect on the growth and acid-production of vaginal lactobacilli, the vaginal flora and vaginal acidity were not restored to a desired extent, 7/15 cases had an Nugent score of the vaginal flora ≤3.

Group III: the composition comprising maltose and 0.2% sodium benzoate also had a strong inhibition effect on vaginal fungi, and the incidence of overgrowth of fungi was lower after using it (2/15); however, vaginal lactobacilli was not restored to a desired extent, 10/15 cases had an Nugent score of the vaginal flora ≤3.

Group IV: the composition comprising maltose and 0.1% sodium benzoate had a weak inhibition effect on vaginal fungi, and the incidence of overgrowth of fungi was high (4/16); the inhibition effect on vaginal lactobacilli is weak, vaginal lactobacilli was restored to a desired extent, 13/16 cases had an Nugent score of the vaginal flora ≤3, after the administration of the composition, vulvovaginal pruritus was significantly alleviated, leucorrhea decreased, and fishy smell disappeared in the patients.

Group V: the composition of the present invention comprising 0.1% sodium benzoate, 0.005% sodium dehydroacetate, and maltose had a strong inhibition effect on fungi, and the incidence of overgrowth of vaginal fungi was lower after using it (1/15); the inhibition effect on lactobacilli is weak, after administration of the composition for 3~4 days, vaginal lactobacilli and vaginal acidity could be restored, 13/15 cases had an Nugent score ≤3; vulvovaginal pruritus was significantly alleviated, leucorrhea decreased, and fishy smell disappeared in the patients.

Group VI: the composition of the present invention free of saccharide were incapable of promoting the growth of vaginal lactobacilli and the acid production; in the patients suffering from Bacterial vaginosis, vaginal lactobacilli and vaginal acidity were rarely restored; and therefore the composition of the present invention free of saccharide was not suitable for patients suffering from Bacterial vaginosis.

Group VII: the composition of the present invention comprising 0.1% sodium benzoate, 0.1% sodium propionate, and maltose had a strong inhibition effect on vaginal fungi, while had a weak inhibition effect on vaginal lactobacilli; both the vaginal lactobacilli and vaginal acidity were effectively restored after using it, and 12/15 cases had an Nugent score of the vaginal flora ≤3; the incidence of overgrowth of vaginal fungi was lower (1/15). After the administration of the composition, vulvovaginal pruritus was significantly alleviated, leucorrhea decreased, and fishy smell disappeared in the patients.

Group VIII: the composition of the present invention comprising 0.1% sodium benzoate, 0.0125% sorbic acid, and maltose had a strong inhibition effect on vaginal fungi, while had a weak inhibition effect on vaginal lactobacilli; both the vaginal lactobacilli and vaginal acidity were effectively restored after using it, and 11/14 cases had an Nugent score of the vaginal flora ≤3 分; the incidence of overgrowth of vaginal fungi was lower (2/14). After the administration of the composition, vulvovaginal pruritus was significantly alleviated, leucorrhea decreased, and fishy smell disappeared in the patients.

8. Conclusion: sodium benzoate at a concentration effective to significantly inhibit the growth of vaginal fungi, for example, 0.2% sodium benzoate, had a strong inhibition effect on vaginal lactobacilli, sodium benzoate at such a concentration in combination with maltose had a poor effect on the treatment of Bacterial vaginosis; benzoic acid and/or sodium salt thereof in combination with dehydroacetic acid and/or sodium salt thereof, propionic acid and/or a salt thereof, sorbic acid and/or a salt thereof, had a strong inhibition effect on fungi, while had a weak inhibition effect on lactobacilli; lower dose sodium benzoate (such as at a concentration of 0.1%) in combination with maltose not only promotes the growth of vaginal normal lactobacilli, but also significantly reduces the overgrowth and infection of vaginal fungi, and therefore are suitable for clinical treatment.

TABLE 3

The effect of the compositions of present invention on Bacterial vaginosis

| | Before administration | Day 1 | Day 2 | Day 3 | Day 4 | Day 5 | Note |
|---|---|---|---|---|---|---|---|
| Group I Saccharides, free of sodium benzoate | | | | | | | |
| pH 4.2~4.5 | 0/14 | 4/14 | 2/14 | 1/14 | 2/14 | 1/14 | 1 case still had a pH |
| pH 3.8~4.1 | 0/14 | 6/14 | 6/14 | 7/14 | 6/14 | 7/14 | higher than 4.5; 5 case |
| pH <3.8 | 0/14 | 1/14 | 3/14 | 4/14 | 5/14 | 5/14 | had a pH lower than |
| Nugent ≤3 | 0/14 | 5/14 | 10/14 | 11/14 | 13/14 | 13/14 | 3.8; the cases with |
| symptom alleviated/eliminated | 0/14 | 10/14 | 11/14 | 13/14 | 10/14 | 7/14 | growth of fungi were in a high proportion, and |
| *Candida* | 0/15 | 0/15 | 5/14 | 6/14 | 9/14 | 9/14 | their symptoms were alleviated at first but aggravated latter. |
| Group II saccharides + 0.5% sodium benzoate | | | | | | | |
| pH 4.2~4.5 | 0/15 | 0/15 | 2/15 | 4/15 | 6/15 | 6/15 | 6 cases still had a pH |
| pH 3.8~4.1 | 0/15 | 0/15 | 0/15 | 1/15 | 2/15 | 3/15 | higher than 4.5; the |
| pH <3.8 | 0/15 | 0/15 | 0/15 | 0/15 | 0/15 | 0/15 | restoration of Nugent |
| Nugent ≤3 | 0/15 | 0/15 | 1/15 | 3/15 | 5/15 | 7/15 | scores were all lower |
| symptom alleviated/eliminated | 0/15 | 7/15 | 6/15 | 9/15 | 8/15 | 11/15 | than 50%; the symptoms were |
| *Candida* | 0/15 | 0/15 | 0/15 | 0/15 | 0/15 | 0/15 | partially improved; no cases had growth of fungi. |
| Group III saccharides + 0.2% sodium benzoate | | | | | | | |
| pH 4.2~4.5 | 0/15 | 3/15 | 2/15 | 5/15 | 5/15 | 6/15 | 2 cases still had a pH |
| pH 3.8~4.1 | 0/15 | 0/15 | 1/15 | 2/15 | 4/15 | 7/15 | higher than 4.5; Nugent |

TABLE 3-continued

The effect of the compositions of present invention on Bacterial vaginosis

| | Before administration | Day 1 | Day 2 | Day 3 | Day 4 | Day 5 | Note |
|---|---|---|---|---|---|---|---|
| pH <3.8 | 0/15 | 0/15 | 0/15 | 0/15 | 0/15 | 0/15 | score was restored; the |
| Nugent ≤3 | 0/15 | 3/15 | 3/15 | 4/15 | 8/15 | 10/15 | symptoms were |
| symptom alleviated/eliminated | 0/15 | 10/15 | 11/15 | 12/15 | 13/15 | 13/15 | significantly improved; cases with growth of |
| Candida | 0/15 | 0/15 | 0/15 | 2/15 | 1/15 | 2/15 | fungi appeared. |
| Group IV saccharides + 0.1% sodium benzoate | | | | | | | |
| pH 4.2~4.5 | 0/16 | 2/16 | 5/16 | 4/16 | 3/16 | 2/16 | 2 cases still had a pH |
| pH 3.8~4.1 | 0/16 | 2/16 | 3/16 | 7/16 | 8/16 | 9/16 | higher than 4.5; 3 cases |
| pH <3.8 | 0/16 | 0/16 | 1/16 | 2/16 | 2/16 | 3/16 | had a pH lower than |
| Nugent ≤3 | 0/16 | 3/16 | 7/16 | 10/16 | 12/16 | 13/16 | 3.8, Nugent score was |
| symptom alleviated/eliminated | 0/16 | 11/16 | 13/16 | 14/16 | 12/16 | 12/16 | significantly restored; the symptoms were |
| Candida | 0/16 | 0/16 | 2/16 | 1/16 | 3/16 | 4/16 | significantly improved; more cases had growth of fungi. |
| Group V Saccharides + 0.1% sodium benzoate + 0.005% sodium dehydroacetate | | | | | | | |
| pH 4.2~4.5 | 0/15 | 2/15 | 3/15 | 2/15 | 3/15 | 3/15 | 2 cases still had a pH |
| pH 3.8~4.1 | 0/15 | 2/15 | 2/15 | 4/15 | 7/15 | 9/15 | higher than 4.5, and |
| pH <3.8 | 0/15 | 0/15 | 0/15 | 1/15 | 1/15 | 1/15 | Nugent score was |
| Nugent ≤3 | 0/15 | 2/15 | 3/15 | 5/15 | 10/15 | 13/15 | significantly restored; |
| symptom alleviated/eliminated | 0/15 | 9/15 | 10/15 | 13/15 | 14/15 | 14/15 | the symptoms were significantly improved |
| Candida | 0/15 | 0/15 | 0/15 | 0/15 | 1/15 | 1/15 | or eliminated; and the incidence of Candida cases was low. |
| Group VI 0.1% sodium benzoate + 0.005% sodium dehydroacetate | | | | | | | |
| pH 4.2~4.5 | 0/10 | 0/10 | 1/10 | 0/10 | 1/10 | 1/10 | 9 cases still had a pH |
| pH 3.8~4.1 | 0/10 | 0/10 | 0/10 | 1/10 | 0/10 | 0/10 | higher than 4.5; Nugent |
| pH <3.8 | 0/10 | 0/10 | 0/10 | 0/10 | 0/10 | 0/10 | score was not |
| Nugent ≤3 | 0/10 | 0/10 | 0/10 | 0/10 | 1/10 | 1/10 | significantly improved. |
| symptom alleviated/eliminated | 0/10 | 0/10 | 1/10 | 0/10 | 1/10 | 0/10 | |
| Candida | 0/10 | 0/10 | 0/10 | 0/10 | 0/10 | 0/10 | |
| Group VII Saccharides + 0.1% sodium benzoate + 0.1% sodium propionate | | | | | | | |
| pH 4.2~4.5 | 0/15 | 2/15 | 1/15 | 2/15 | 3/15 | 2/15 | 2 cases still had a pH |
| pH 3.8~4.1 | 0/15 | 1/15 | 3/15 | 3/15 | 6/15 | 9/15 | higher than 4.5; Nugent |
| pH<3.8 | 0/15 | 0/15 | 1/15 | 0/15 | 1/15 | 2/15 | score was significantly |
| Nugent ≤3 | 0/15 | 2/15 | 3/15 | 4/15 | 8/15 | 12/15 | restored; the symptoms |
| symptom alleviated/eliminated | 0/15 | 8/15 | 8/15 | 11/15 | 10/15 | 13/15 | were significantly improved; the incidence |
| Candida | 0/15 | 0/15 | 0/15 | 0/15 | 0/15 | 1/15 | of growth of fungi was low. |
| Group VIII Saccharides + 0.1% sodium benzoate + 0.0125% sorbic acid | | | | | | | |
| pH 4.2~4.5 | 0/14 | 3/14 | 3/14 | 2/14 | 3/14 | 2/14 | 4 cases still had a pH |
| pH 3.8~4.1 | 0/14 | 1/14 | 2/14 | 5/14 | 7/14 | 8/14 | higher than 4.5; Nugent |
| pH <3.8 | 0/14 | 0/14 | 0/14 | 1/14 | 2/14 | 1/14 | score was significantly |
| Nugent ≤3 | 0/14 | 2/14 | 3/14 | 4/14 | 7/14 | 11/14 | restored; the symptoms |
| symptom | 0/14 | 8/14 | 7/14 | 10/14 | 11/14 | 13/14 | were significantly |

TABLE 3-continued

The effect of the compositions of present invention on Bacterial vaginosis

|  | Before administration | Day 1 | Day 2 | Day 3 | Day 4 | Day 5 | Note |
|---|---|---|---|---|---|---|---|
| alleviated/eliminated Candida | 0/14 | 0/14 | 0/14 | 1/14 | 1/14 | 2/14 | improved; the incidence of growth of fungi was low. |

Note:
vaginal pH ≤4.5 for normal, representing that vaginal acidity is within a normal range; pH >4.5 for abnormal, representing that vaginal acidity is reduced;
Nugent score ≤3, representing normal vaginal flora; Nugent score >3, representing abnormal vaginal flora; The concrete scoring methods could be found in Guidance for Industry: Bacterial Vaginosis-Developing antimicrobial Drugs for Treatment. FDA, 1998.
No Candida is observed for normal, i.e., "0"; Candida observed suggests overgrowth, i.e., abnormal.

Experimental Example IV

Experimental object: observing the composition comprising sodium benzoate and organic acid preservatives as active ingredients had therapeutic effect on cytolytic vaginosis. Unless otherwise illustrated, the solutions in the experiments are all aqueous solutions.

1. Experimental agents: the composition of the present invention (i.e., the composition of Example 5) comprising 0.1% (w/v) sodium benzoate and 0.0125% (w/v) sodium dehydroacetate.

2. Experimental cases:
20 cases were enrolled in the group, wherein the cases had recurrent symptoms, such as vulvovaginal pruritus or vulvovaginal burning pain, and increased leucorrhea, the pH value of vaginal secretion <4.1, vaginal bacteria were dominated by large Gram-positive rods, and Candida spores or hypha were not found, the epithelial cells of vaginal mucosa were broken, and naked nucleus were found.
3. Omission of cases: the cases, which failed to complete the treatment course, failed to reexamination, or washed vagina with or administrated with antibacterial agents during the observation, were omitted cases and were excluded from tests.
4. Experimental methods: the patients in the group were administrated topically in vagina with 5 g of the composition of the present invention twice per day for consecutive 5 days, wherein the patients were at least administrated by the doctor once a day; the pH value of vaginal secretion was determined, microscopic examination of the stained secretion smear was conducted, the bacterial number and form were observed, and Nugent scoring was conducted.

5. Observed results: the omitted cases were excluded, observing changes in vulvovaginal pruritus, vulvovaginal burning pain and leucorrhea state, the pH value of vaginal secretion, observing the Nugent scores of the vaginal flora, whether there were naked nucleus or not.

6. Experimental result: as shown in Table 4:

TABLE 4

The effect of the compositions on Candidal vaginitis/Cytolytic vaginosis

|  |  | Before administration | Day 1 | Day 2 | Day 3 | Day 4 | Day 5 | Result assessment |
|---|---|---|---|---|---|---|---|---|
| Cytolytic vaginosis | symptom alleviated/ eliminated | 0/19 | 7/19 | 8/19 | 13/19 | 17/19 | 17/19 | After the administration of the composition, the symptoms were significantly improved; vaginal pH was enhanced; naked nucleuses and cellular fragments were significantly decreased. |
|  | pH 4.2~4.5 | 0/19 | 3/19 | 5/19 | 9/19 | 8/19 | 10/19 |  |
|  | pH 3.8~4.1 | 6/19 | 5/19 | 8/19 | 9/19 | 11/19 | 9/19 |  |
|  | pH <3.8 | 13/19 | 11/19 | 6/19 | 1/19 | 0/19 | 0/19 |  |
|  | cellular fragments/ naked nucleus | 19/19 | 10/19 | 10/19 | 6/19 | 3/19 | 1/19 |  |

Note:
symptom improved/eliminated: discomforts such as vulvovaginal pruritus and vulvovaginal burning pain are significantly improved or eliminated, leucorrhea decreases, with very few or without bean curd slag-like clots. The normal pH range of vagina is from 3.5 to 4.5, preferably 3.8~4.1. When the pH is below 3.8, the acidity is over-enhanced. Fragments of broken vaginal mucosa epithelial cells/naked nucleus: normal for negative.

After the administration of the composition of the present invention, the acid production of lactobacilli was significantly inhibited, vaginal pH increased to above 3.8, the vaginal acidity was reduced, cytolysis was inhibited, and therefore the fragments and naked nucleus produced by cytolysis of epithelial cells were significantly decreased. After the administration of the composition of the present invention, the symptoms such as vulvovaginal pruritus and vulvovaginal burning pain were quickly alleviated or even eliminated, and leucorrhea decreased in the patients.

8. Conclusion: the composition of the present invention inhibited pathogenic vaginal lactobacilli, inhibited the abnormal enhancement of vaginal acidity, had a therapeutic effect on cytolytic vaginosis and lactobacillosis, quickly alleviated or even eliminated the symptoms such as vulvovaginal pruritus and vulvovaginal burning pain, and significantly decreased the leucorrhea in the patients.

Experimental Example Typical Case I

A patient, a female of 28 year old, had vulvovaginal pruritus, increased leucorrhea, and algopareunia for 3 months, and was diagnosed as "Candidal vaginitis" in hospital. She was treated with many antifungal agents. However, the symptoms were alleviated during administration, but reoccurred after administration. The inventors conducted examination by taking vaginal swab, and found that the pH value of vaginal secretion was below 3.8. By secretion smearing, Gram-staining and microscopic observation, the vaginal flora was large Gram-positive rods without observing fungal spores and hypha, the epithelial cells of vaginal mucosa were not intact and were cytolyzed and broken, and naked nucleus were found. Thus, the patient was diagnosed as "cytolytic vaginosis". The patient was administrated topically in vagina with 4 mg of the composition of Example 2, once per day for consecutive 5 days. Vulvovaginal pruritus disappeared and leucorrhea decreased in the patient, the pH value of vaginal secretion obtained again by vaginal swab was 4.1, the vaginal flora still was dominant large Gram-positive rods, no broken vaginal mucosa epithelial cells and naked nucleus were found. The result showed: the composition of the present invention comprising sodium benzoate and sodium dehydroacetate as active ingredients had a therapeutic effect on cytolytic vaginosis.

Experimental Example Typical Case II

A patient, a female of 26 year old, had recurrent vulvovaginal pruritus, vulvovaginal burning pain and increased leucorrhea for one year, and was diagnosed as Candidal vaginitis in hospital. The symptoms were improved during administration, but reoccurred after administration. The inventors conducted examination by taking vaginal swab, and found that the pH value of vaginal secretion was below 3.8. By secretion smearing, Gram-staining and microscopic observation, the vaginal flora was large Gram-positive rods with a long body, fungal spores and hypha were found, and the cytolyzed and broken epithelial cells were found occasionally. Thus, the patient was diagnosed as "Candidal vaginitis". The patient was administrated topically in vagina with 4 ml of the composition of Example 8, once per day for consecutive 5 days. The patient's symptoms such as vulvovaginal pruritus and vulvovaginal burning pain disappeared, and leucorrhea decreased significantly, the pH value of vaginal secretion obtained again by vaginal swab was about 4.1, the vaginal flora still was dominant large Gram-positive rods but with a short body, no fungal spores and hypha were found. The result showed that the composition of the present invention comprising sodium benzoate and sodium propionate as active ingredients had a therapeutic effect on Candidal vaginitis.

Experimental Example Typical Case III

A patient, a female of 31 year old, had vulvovaginal pruritus and leucorrhea with fishy smell for a year. The patient had increased leucorrhea with fishy smell with no apparent causes a year ago, the symptoms got severe after sexual intercourse, when the symptoms got severe, the patient sometime could not fall asleep with vulvovaginal pruritus. She was treated with many antifungal agents and many lotions in hospital. However, the symptoms were alleviated during administration, but reoccurred after administration. The inventors applied the leucorrhea to the smearing and staining examination. A large amount of Gram-negative rods, negative cocci and positive cocci were found in different forms, no large Gram-positive rods were found, and the leukocyte was rare. The pH of leucorrhea was determined to be 5.4. Thus, the patient was diagnosed as bacterial vaginosis. The patient was administrated topically in vagina with 5 g of the gel as made in Example 5, twice per day. The patient's vulvovaginal pruritus and abnormal odor in leucorrhea were significantly alleviated a day after administration, and the pH value of vaginal secretion obtained again was 4.6. Leucorrhea decreased, and abnormal odor in leucorrhea and vulvovaginal pruritus disappeared two days after the administration, and the pH value of vaginal secretion obtained again was 4.1. By secretion smearing, Gram-staining and microscopic observation again, the bacteria were dominated by Gram-positive rods, and negative rods, while the cocci were rare. The patient was administrated continuously to complete the treatment course. The symptoms did not reoccur three months after administration.

REFERENCE DOCUMENTS

1. Deutchman, et al. Vaginitis: Diagnosis Is the Key. *Patient Care* 2 (Sep. 15, 1994): 39-61.
2. MARI E. EGAN, et al. Diagnosis of Vaginitis. American family physician. (Sep. 1, 2000, http://www.aafp.org/afp/20000901/1095.html)
3. Encyclopedia on Pharmaceutical Adjuvants, edited by Ruo Mingsheng and Gao Tianhui, Sichuan Science and Technology Press, published in 2006, page 1084;
4. Encyclopedia on Pharmaceutical Adjuvants, edited by Ruo Mingsheng and Gao Tianhui, Sichuan Science and Technology Press, published in 2006, page 1087;
5. National non-prescription drugs Handbook, edited by Wu Jingshi, the second edition, People's Medical Publishing House, published on May 2004, page 129;
6. Current Structured Drugs, edited by Wang Zhemin, Beijing Science and Technology Press, published in 1993, page 270;
7. Mold Prevention in Industry, edited by Ma Zhenying and Wu Xiaomei, Light Industry Press, published in October 1983, page 134;
8. Food preservation and Food preservatives, edited by Wang Suying, Li Lin, and Wang Huijun, China Light Industry Press, published in March 1998, page 240, Table 7-2;
9. Pharmaceutics, edited by Xi Nianzhu and Gu Xueqiu, the second edition (1990), People's Medical Publishing House, pages 292-349;
10. Pharmaceutics, edited by Xi Nianzhu and Gu Xueqiu, the second edition (1990), People's Medical Publishing House, pages 377-386;
11. U.S. FDA, Federal Register/Vol. 48, No. 199, 46704/Oct. 12, 1983/Proposed Rules.

The invention claimed is:

1. A vaginal composition for inhibiting vaginal fungi, comprising the following:
   (1) benzoic acid and/or sodium salt thereof, the total concentration of which, calculated based on sodium benzoate, is 0.025-0.2% (w/v);
   (2) dehydroacetic acid and/or sodium salt thereof, wherein the total concentration of the dehydroacetic acid and/or sodium salt thereof, calculated based on sodium dehydroacetate, is 0.005-0.025% (w/v);
   (3) an ointment matrix or water;
   (4) the pH value of the composition is from 3.5 to 6.5;

wherein the composition is packaged in the form of one of a sterilized and sealed single dose package, a vagina use device, or a disposable vagina use device.

2. The composition according to claim 1, further comprising 0.001~0.5 mg metronidazole or tinidazole per unit dosage form.

3. The composition according to claim 1, further comprising one or more estrogens, selected from the group consisting of stilbestrol, estradiol and/or estriol, at a total amount of 0.01~3 mg per unit-dosage form.

4. A method for inhibiting vaginal fungi, comprising intravaginal administration of an effective amount of the composition of claim 1 to a female in need thereof.

5. The composition according to claim 1, the composition further comprising 0.01~0.25 mg metronidazole or tinidazole per unit dosage form.

6. The composition according to claim 1, wherein the composition further comprises estriol.

7. The vaginal composition according to claim 1, wherein the total concentration of benzoic acid and/or sodium salt thereof is 0.05~0.125% (w/v) calculated based on sodium benzoate.

8. The vaginal composition according to claim 1, wherein the ointment matrix is non-flowable, viscous, water-soluble gel matrix.

9. The vaginal composition according to claim 1, wherein the ointment matrix comprises Xanthan gum.

10. The vaginal composition according to claim 1, wherein the pH value of the composition is from 3.5 to 6.5.

11. The vaginal composition according to claim 1, wherein the composition is in the form of a sterilized and sealed single dose package.

12. The vaginal composition according to claim 1, wherein the pH value of the composition is from 4.0 to 5.5.

13. The vaginal composition according to claim 1, further comprising propionic acid and/or a salt thereof, and the total concentration of propionic acid and/or a salt thereof, calculated based on sodium propionate is 0.05~1.0% (w/v).

14. The vaginal composition according to claim 13, wherein the total concentration of propionic acid and/or a salt thereof is 0.1~0.5% (w/v) calculated based on sodium propionate.

* * * * *